United States Patent [19]

McRae

[11] Patent Number: Plant 6,504

[45] Date of Patent: Jan. 3, 1989

[54] HYBRID ORIENTAL LILY NAMED SYLVIA

[75] Inventor: Edward A. McRae, Boring, Oreg.

[73] Assignee: Melridge, Inc., Gresham, Oreg.

[21] Appl. No.: 38,762

[22] Filed: Apr. 15, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new variety of hybrid Oriental lily plant having large upright-facing flowers particularly characterized by their generally pink coloration with deeper pink midribs and with the outer tepals having very much ruffled margins, the flowers in general being of excellent form and long persistence both on the plant and as cut flowers. The large size and substance and the upright to semi-upright orientation of the flowers of this variety, in combination, is completely new in the Oriental hybrid divisions of lilies suited to forcing and to mass commercial cultivation.

1 Drawing Sheet

BACKGROUND OF THE NEW PLANT

My new variety of lily plant originated as a seedling which first flowered in Sandy, Oreg., in 1970 among a group of seedlings planted by me with the object of producing large flowered upright and semi-upright Oriental hybrids in shades of pink and white suited to forcing into flower out-of-season, heretofore unknown in the lily breeding art. The mother plant of these seedlings was a selected clone from the strain 'Pink Glory' and the pollen parent was a selected form of the species *Lilium nobilissimum;* the cross of these distantly related lilies having been successfully accomplished by maintaining extremely high greenhouse temperatures for more than one week after pollination.

This particular seedling was selected for propagation because its flowers were characterized by an upright to semi-upright orientation, extremely large size and broad tepalled "bowl-shaped" form, and a distinctive clear pink coloration with richer magenta-rose midribs, unique among Oriental hybrid lilies. This selected seedling was asexually reproduced by me and under my direction at Sandy, Oregon, with such success that successive generations were produced by natural propagation from bulblets, by bulb scale propagation, and by tissue culturing from bulb scale explants. The successive generations of this new variety demonstrated that the novel and distinctive characteristics of the selected seedling hold true, under asexual propagation, from generation to generation and appear to be firmly fixed.

This new plant has been found to possess unusually strong, stout stems with exceptionally broad leaves and in addition, the clone has been found to possess to a high degree the desirable characteristics of hybrid vigor, great hardiness, and disease resistance. In addition, it has been found that the new plant possesses all of the desired characteristics of excellence of form, color and habit.

The new plant has also been shown to be well suited to forcing out-of-season when the bulbs are dug at the appropriate time and properly precooled. For example, late October-dug bulbs, properly precooled and potted in January, will flower under glass in western Oregon in an average of one hundred to one hundred fifteen days with no supplementary lighting and at moderate greenhouse temperatures.

DESCRIPTION OF THE DRAWING

This new variety of lily plant is illustrated by the accompanying photographic drawing which, in full color, shows the open bloom and illustrates the flower form, tepal arrangement and, in particular, the novel and distinctive flower size, form and its generally upright orientation, the color rendition being as close to that specified as is reasonably possible to obtain by professional photographic procedures.

DESCRIPTION OF THE NEW VARIETY

The following is a detailed description of my new variety of hybrid Oriental lily, with nomenclature according to The International Lily Register of The Royal Horticultural Society of London (Second Edition, 1969); and with color designations according to The R.H.S. Colour Chart of The Royal Horticultural Society published by the society in 1966.

THE PLANT

Origin: Seedling.

Parentage:

- *Seed parent.*—A selected clone from the 'Pink Glory' strain (unpatented).
- *Pollen parent.*—A selected clone of *Lilium nobilissimum* (unpatented).

Classification:

- *Horticultural.*—Division VII-B, Bowl-shaped Oriental Hybrid Lily, according to The Horticultural Classification of Lilies by The Royal Horticultural Society of London.
- *Commercial.*—Hybrid Lilium Clone.

Form: Single stem, erect and stately.

Height: About 70 to 125 cm., according to age, from bulbs of about 14 to 18 cm. in circumference, provided that their light levels are adequate. Low light levels may cause "stretching".

Growth: Vigorous and upright.

Foliage:

- *Quantity.*—Abundant
- *Leaf size.*—Unusually broad, about 7 to 8 cm. wide and about 12 to 15 cm. long.
- *Leaf shape.*—Lanceolate with acuminate tips.
- *Texture.*—Leathery.
- *Aspect.*—Glossy.
- *Color.*—Medium green, lighter on the bottom side.

Bulbs:

*Size.*—Varying according to age and ranging to about 25 cm. in circumference as commercially used.

*Color.*—White with flushes of soft pink or soft yellow after exposure to light.

THE BUD

Form: Long ovoid with obtuse apex.

Size: About 9 to 12 cm. long and about 10 to 12 cm. in circumference just prior to opening.

Opening rate: The bud opens slowly, taking about one hour in response to morning light.

Color: Red purple, 65C-D, with soft green midribs.

Peduncle:

*Length.*—About 4 to 6 cm., in average, but the peduncle may elongate if light levels are too low or if the bulbs have been improperly stored prior to forcing.

*color.*—Medium green with very light plum overlay.

THE FLOWER

Blooming habit: Once annually and profusely in midseason.

Size: Very large, averaging about 18 to 23 cm. in diameter. The tepal tips reflex on the second day leaving a spread of 15 to 18 cm. in diameter.

Borne: As a single raceme having from three to six flowers from a bulb of about 14 to 16 cm. in circumference.

Shape: A broad bowl shape by the second day, the bowl having a depth of about 10 cm.

Tepalage:

*Number.*—Six, imbricated and hexagonally arranged.

*Size.*—Outer tepals — About 3 to 3.5 cm. wide. Inner tepals — About 5 to 5.5 cm. wide.

*Color.*—Generally 65B, shading to 64D, with the midrib of each tepal being a deeper magenta-rose, 64B-C, the pink color suffusing to the margins of the tepals and becoming only slightly lighter, 65B. The basal 10 mm. of the tepals, parallel with the nectaries, is white and the nectary furrows are apple green.

Spotting: The flowers are unspotted.

Color changes: The flowers become slightly larger and a more lavender-toned pink, approaching 65A-C, as the flowers age. Low light levels and extreme heat may cause the pink pigmentation to decrease.

Appearance: The flower is shiny.

Fragrance: Distinct and pleasing.

Pedicel:

*Length.*—About 8 to 12 cm., in average.

*Color.*—Medium green with light plum overlay.

*Form.*—Sturdy and ascending to about 45 degrees from the horizontal.

Disease resistance: The flower and plant are resistant to disease; and, in particular, they are resistant to Fusarium bulb rot and Botrytis blight, as observed in western Oregon.

Lasting quality: The tepals stay on the stems for about three weeks and the flower is long lasting, both on the plant and as a cut flower.

REPRODUCTIVE ORGANS

Stamens:

*Number.*—Six.

*Arrangement.*—Typical of genus Lilium.

*Anthers (Dehisced) and pollen.*—Greyed red, 179A.

*Filaments.*—Length: About 8 to 10 cm. Color: Soft green to white.

Pistil:

*Number.*—One.

*Length.*—About 8 to 10 cm.

*Stigma.*—Size: Large. Color: Soft greenish white to very light pink.

Characteristics of ovary: The ovary is characteristic of genus Lilium.

THE FRUIT

Fertility: The fruit is fertile.

Shape: Ovoid.

Color at maturity: Soft brown, sometimes overlaid with soft plum.

This new variety of Oriental hybrid lily most nearly resembles 'Pink Glory' (unpatented) but it has much larger, thicker and more bowl-shaped flowers which, in orientation, are more upright to semi-upright rather than side-facing. Also, the flowers of the new variety are completely unspotted, and are distinguished by their deeper magenta-rose midribs. The leaves of the new plant are much broader and its stems are stronger and stockier than found in 'Pink Glory'.

The new plant also resembles its sister clone 'Pantomime' (patent pending) but can be distinguished by its only slightly fluter flower margins, anthers which produce much more pollen and dehisce normally, and its tepals having a broader white area at the base.

I claim:

1. The new and distinctive variety of hybrid Oriental lily plant and parts thereof, substantially as herein shown and described, characterized by its unique upright to semi-upright flowers having a clear pink coloration with deeper magenta-rose midribs and by their complete lack of spotting; and by its versatility both as a garden plant and as a cut flower producer when forced under glass out-of-season from precooled bulbs.

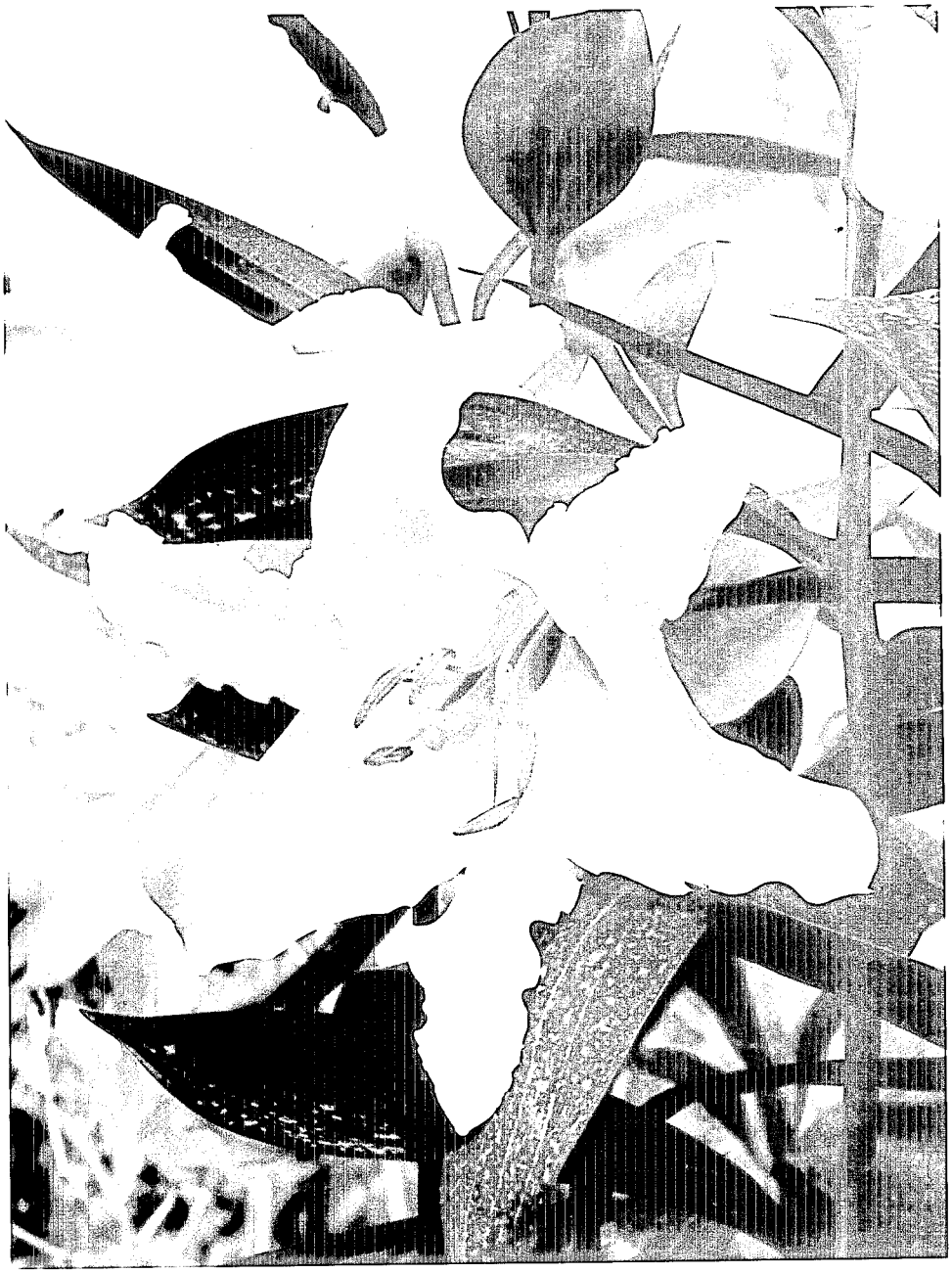

* * * * *